US005756474A

United States Patent [19]
Furstenau

[11] Patent Number: 5,756,474
[45] Date of Patent: May 26, 1998

[54] NON-AQUEOUS ORAL-DRENCH COMPOSITIONS CONTAINING AVERMECTIN COMPOUNDS

[75] Inventor: Kai-Uwe Furstenau, Blacktown, Australia

[73] Assignee: Pfizer, Inc., New York, N.Y.

[21] Appl. No.: 835,454

[22] Filed: Apr. 8, 1997

[30] Foreign Application Priority Data

Apr. 17, 1996 [AU] Australia ................. PN 9333

[51] Int. Cl.$^6$ ................................. A61K 31/70
[52] U.S. Cl. .................................. 514/30
[58] Field of Search ...................... 514/30

[56] References Cited

U.S. PATENT DOCUMENTS

| | | | |
|---|---|---|---|
| 4,201,861 | 5/1980 | Mrozik et al. | 536/17 A |
| 4,206,205 | 6/1980 | Mrozik et al. | 424/180 |
| 4,310,519 | 1/1982 | Albers-Schonberg et al. | 424/181 |
| 4,389,397 | 6/1983 | Lo et al. | 424/180 |
| 4,560,677 | 12/1985 | Dybas | 514/30 |
| 4,607,050 | 8/1986 | Kieran et al. | 514/520 |
| 4,853,372 | 8/1989 | Williams et al. | 514/30 |
| 5,332,577 | 7/1994 | Gertner et al. | 424/449 |
| 5,439,924 | 8/1995 | Miller | 514/345 |

*Primary Examiner*—Kevin E. Weddington
*Attorney, Agent, or Firm*—Peter C. Richardson; Paul H. Ginsburg; Jolene W. Appleman

[57] ABSTRACT

The invention is directed to a novel non-aqueous oral-drench composition comprising from 0.01% to 2.0% (w/v) of an avermectin compound; from 30% to 45% (w/w) of an oil, said oil being selected from the group consisting of corn oil, sunflower oil, peanut oil and safflower oil; from 0.01% to 1.0% (w/v) of an oil-soluble antioxidant; and from 50% to 70% (w/w) of a fatty acid ester, said fatty acid ester being selected from the group consisting of caprylic/capric triglyceride, octyl palmitate and propylene glycol dicaprylate/dicaprate. The invention is further directed to methods of using the non-aqueous composition to treat parasitic diseases in mammals.

14 Claims, No Drawings

NON-AQUEOUS ORAL-DRENCH COMPOSITIONS CONTAINING AVERMECTIN COMPOUNDS

This applicational is a nonprovisional application claiming benefit of Australian provisional application no. PN9333 filed Apr. 17, 1996.

BACKGROUND OF THE INVENTION

The invention relates to novel non-aqueous oral-drench compositions containing avermectin compounds and to methods of using said compositions to treat parasitic diseases. Avermectins are a series of macrocyclic lactones produced by the soil actinomycete, Streptomyces avermitilis. Avermectins are referred to in U.S. Pat. No. 4,310,519, which is incorporated herein by reference. Avermectins are very potent broad-spectrum antiparasitic agents that are useful as anthelmintics, ectoparasiticides, insecticides and acaricides.

Avermectins can be administered orally or parenterally to mammals. While avermectins are generally unstable and insoluble in water, aqueous formulations are often used to administer avermectins. This is because, upon injection, conventional non-aqueous formulations often cause irritation and tissue damage at the injection site, and such formulations generally have higher viscosity and therefore poor syringability. In oral application, aqueous formulations generally taste better and cost less than non-aqueous formulations. Thus, significant effort has been made to dissolve avermectin compounds in aqueous formulations using, for example, various surfactants as described in U.S. Pat. No. 4,389,397.

Due to the instability and insolubility of avermectin compounds in aqueous formulations, a suitable non-aqueous formulation remains desirable. While non-aqueous formulations have been developed for parenteral administration, such formulations are generally not suitable for oral administration. For example, U.S. Pat. No. 4,853,372 refers to a parenteral formulation comprising ivermectin (an avermectin compound) dissolved in propylene glycol and glycerol formal. If administered orally, such a formulation could cause severe irritation in animals because propylene glycol is known to cause ataxia and hemoglobinuria in certain animals such as sheep. Thus, an advantage of the novel non-aqueous avermectin composition of the present invention is that it is suitable for oral-drench administration.

SUMMARY OF THE INVENTION

The invention is directed to a non-aqueous oral-drench composition comprising from 0.01% to 2.0% (w/v) of an avermectin compound; from 30% to 45% (w/w) of an oil, said oil being selected from the group consisting of corn oil, sunflower oil, peanut oil and safflower oil; from 0.01% to 1.0% (w/v) of an oil-soluble antioxidant; and from 50% to 70% (w/w) of a fatty acid ester, said fatty acid ester being selected from the group consisting of caprylic/capric triglyceride, octyl palmitate and propylene glycol dicaprylate/dicaprate.

The invention is also directed to a method of treating a parasitic disease in a mammal comprising orally administering to a mammal in need of such treatment an effective amount of said non-aqueous composition, referred to above.

The term "avermectin" or "avermectin compound", as used herein, unless otherwise indicated, includes each of the avermectin compounds referred to in U.S. Pat. No. 4,310,519, referred to above, as well as any other avermectin derivative or analog. The avermectin compounds referred to in U.S. Pat. 4,310,519 have the following structure:

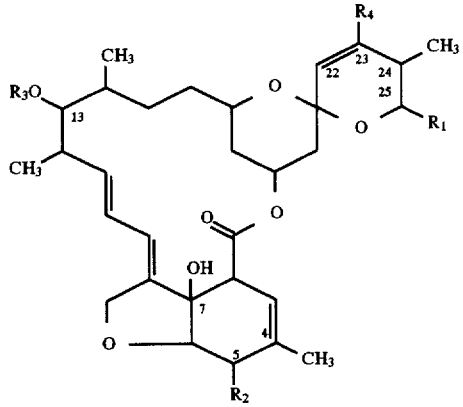

wherein the broken lines indicates a single or double bond, $R_1$ is iso-propyl or sec-butyl;

$R_2$ is methoxy or hydroxy;

$R_4$ is hydroxy when the broken line indicates a single bond and hydrogen when the broken line indicates a double line; and, $R_3$ is the 4'-(alpha-L-oleandrosyl)-alpha-L-oleandrosyl group of the formula:

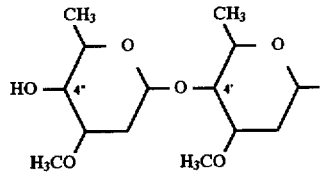

The individual avermectin compounds referred to in U.S. Pat. No. 4,310,519 are set forth below:

| Avermectin | $R_4$/Broken line | $R_1$ | $R_2$ |
|---|---|---|---|
| A1a | H/double bond | sec-butyl | methoxy |
| A1b | H/double bond | iso-propyl | methoxy |
| A2a | OH/single bond | sec-butyl | methoxy |
| A2b | OH/single bond | iso-propyl | methoxy |
| B1a | H/double bond | sec-butyl | hydroxy |
| B1b | H/double bond | iso-propyl | hydroxy |
| B2a | OH/single bond | sec-butyl | hydroxy |
| B2b | OH/single bond | iso-propyl | hydroxy |

Derivative compounds include those wherein the 22,23 double bond of the avermectin compounds referred to in U.S. Pat. No. 4,310,519 is selectively reduced to form the 22,23 dihydro compound as disclosed in 4,199,569. Other derivative compounds include the monosaccharide and aglycone compounds referred to in U.S. Pat. No. 4,206,205 wherein $R_3$ of the above structure is hydrogen or alpha-L-oleandrosyl. Other derivative compounds include the acylated derivatives referred to in U.S. Pat. No. 4,201,861 wherein an acyloxy group is present at the $R_4$, $R_2$, $R_3$, 4' or 4" position of the above structures, and the 13-deoxy aglycone compounds referred to in U.S. Pat. Nos. Re. 32,034 and Re. 32,006. Still other avermectin compounds are referred to in U.S. Pat. Nos. 4,427,663, 5,089,480, and 5,411,946. Preferably, the avermectin compound to be used in the present invention is doramectin which is disclosed in U.S. Pat. No. 5,089,480 in Example 18, Table 1, as 25-cyclohexyl-avermectin B1.

DETAILED DESCRIPTION OF THE INVENTION

The avermectin compounds to be used in the non-aqueous oral-drench composition of the present invention are referred to in the literature. U.S. Pat. No. 4,310,519, referred to above, describes the isolation and purification of various avermectin compounds. The structure and preparation of the preferred avermectin compound, doramectin, is disclosed in U.S. Pat. No. 5,089,480, which is herein incorporated by reference. The preparation of another avermectin compound, ivermectin, is referred to in U.S. Pat. No. 4,199,569, which is also incorporated herein by reference. Other avermectin compounds can be prepared according to one or more of the methods disclosed in U.S. Pat. Nos. 4,206,205, 4,201,861 4,427,663, 5,411,946, Re. 32,006 and Re. 32,034. The avermectin compound constitutes from about 0.01% to 2.0% (w/v), preferably 0.05% to 0.2% (w/v), of the final formulation.

The preparation of the non-aqueous composition of the present invention generally begins with the dissolution of the avermectin compound in the fatty acid ester. The dissolution of the avermectin compound is facilitated by the application of gentle agitation and moderate heat (temperature of 40°–45° C.). The fatty acid ester constitutes from about 50% to 70% (w/w), preferably 55% to 65% (w/w), of the final formulation. The fatty acid ester is selected from the group consisting of caprylic/capric triglyceride, octyl palmitate, and propylene glycol dicaprylate/dicaprate. Such fatty acid esters are available from a variety of commercial sources. Caprylic/capric triglyceride is manufactured and sold by Croda Singapore Pte Ltd, Singapore, under the trademark CRODAMOL GTCC. Octyl palmitate is manufactured and sold by ISP van Dyk, Inc. (Belleville, N.J.) under the trademark CERAPHYL 368, and by Croda Universal Ltd (Leek, England) under the trademark CRODAMOL OP. Propylene glycol dicaprylate/ dicaprate is manufactured and sold by Hüls Troisdorf AG (Witten, Germany) under the trademark MIGLYOL 840, and by Henkel KGaA (Düsseldorf, Germany) under the trademark MYRITOL PC. The fatty acid ester improves the solubilisation of the avermectin compound in the composition and is useful for adjusting the viscosity of the composition. Two or more fatty acid esters can be used to optimize the solubility of the avermectin compound and the viscosity of the composition. The viscosity of the final composition should be adjusted to within about 35 to 300 centistokes, preferably within 45 to 80 centistokes. This preferred viscosity range is particularly suited for oral administration of the composition in conventional drenching equipment.

Following the dissolution of the avermectin compound in the fatty acid ester, an oil is added to the composition at ambient temperature (22°–25° C.) with stirring. The oil constitutes from about 30% to 45% (w/w), preferably 35% to 40% (w/w), of the final formulation. The oil is selected from the group consisting of corn oil, sunflower oil, peanut oil and safflower oil. The preferred edible oil is corn oil. As with the other components of the composition of the present invention, more than one type of oil can be combined the make up the oil component of the composition.

As a final step, an oil-soluble antioxidant is added to the composition at ambient temperature with stirring. The oil-soluble antioxidant is added in an amount ranging from about 0.01% to 1.0% (w/v), preferably 0.1% to 0.5% (w/v), of the final composition. The oil-soluble antioxidant improves the stability of the composition by counteracting potential triggers of drug degradation. Examples of oil-soluble antioxidants include butylated hydroxyanisole (BHA) and butylated hydroxytoluene (BHT). Butylated hydroxyanisole is the preferred antioxidant.

Since the composition of the present invention is non-aqueous, and therefore cannot support microbial growth, the addition of preservatives to the formulation is not necessary.

Mammals that can be treated with the composition of the present invention include sheep, cattle, horses, deer, dogs, cats, and pigs. The composition of the present invention is particularly suited for the treatment of sheep and cattle.

The non-aqueous composition of the present invention can be administered to a mammal, preferably an animal, through conventional oral drench equipment.

The intrinsic lubrication properties of the oily components of the non-aqueous composition reduce the friction of the piston seals and valves in conventional drenching equipment and thereby facilitate accurate filling of the measuring chamber and reduce hand fatigue in the user of the equipment. The preferred drenching applicators are the automatic-type applicators that draw the drench solution into a filling chamber of adjustable volume and dispense the metered formulation through a nozzle into the mouth of the subject to be treated.

The non-aqueous composition of the present invention is highly effective against a variety of parasites including gastro-intestinal roundworms, lungworms, sucking lice, and mange mites. In general, the avermectin compound in the non-aqueous composition should be administered at a single dose ranging from about 100 to 300 micrograms per kilogram body weight of subject to be treated. The preferred single dose is 150 micrograms per kilogram body weight of subject to be treated. The single dose can be administered daily.

When a composition containing avermectin compounds is administered orally, or by other means, there is always the possibility that a portion of the composition may spill onto the ground. It is known that doramectin, and other avermectin compounds, are potentially toxic to certain aquatic species, such as Daphnia, at concentrations as low as 25 parts per trillion (ppt). When the non-aqueous composition of the present invention is accidentally spilled, the hydrophobic nature of the composition enhances the tendency of the avermectin to bind to soil and remain at the site of the spill. Thus; there is less of a chance that the composition will seep into the ground water and ultimately into local aquatic systems.

The safety of the non-aqueous composition of the present invention in mammals was established by orally dosing sheep with a placebo dose of the composition (composition that does not contain an avermectin composition) at 10 times the expected target dose. No adverse physiological manifestations were observed during a 10-day monitoring period. In addition, it is believed that degradation of the non-aqueous composition in the sheep resulted in the production of natural fat products of triglyceride structure and fatty acids which became a nutrient source for the rumen micro flora of the sheep.

The compositions described in the following examples were prepared as described above. While the avermectin compound recited in the following examples is doramectin, it should be understood that other avermectin compounds can likewise be used in the compositions specifically described. In the following examples, the term "BHA" means butylated hydroxyanisole. The specific gravity of the compositions recited in the examples typically ranges from 0.89 to 0.91 g/ml at 25° C.

EXAMPLE 1

| | |
|---|---|
| Doramectin | 0.1% w/v |
| BHA | 0.5% w/v |
| Octyl Palmitate | 40% w/w |
| Caprylic/Capric Triglyceride | 20% w/w |
| Corn Oil | q.s. 100% w/v |

EXAMPLE 2

| | |
|---|---|
| Doramectin | 0.1% w/v |
| BHA | 0.5% w/v |
| Octyl Palmitate | 40% w/w |
| Propylene Glycol Dicaprylate/Dicaprate | 20% w/w |
| Corn Oil | q.s. 100% w/v |

EXAMPLE 3

| | |
|---|---|
| Doramectin | 0.2% w/v |
| BHA | 0.5% w/v |
| Octyl Palmitate | 40% w/w |
| Caprylic/Capric Triglyceride | 20% w/w |
| Corn Oil | q.s. 100% w/v |

EXAMPLE 4

| | |
|---|---|
| Doramectin | 0.2% w/v |
| BHA | 0.5% w/v |
| Octyl Palmitate | 40% w/w |
| Propylene Glycol Dicaprylate/Dicaprate | 20% w/w |
| Corn Oil | q.s. 100% w/v |

EXAMPLE 5

| | |
|---|---|
| Doramectin | 0.075% w/v |
| BHA | 0.5% w/v |
| Octyl Palmitate | 40% w/w |
| Caprylic/Capric Triglyceride | 20% w/w |
| Corn Oil | q.s. 100% w/v |

EXAMPLE 6

| | |
|---|---|
| Doramectin | 0.075% w/v |
| BHA | 0.5% w/v |
| Octyl Palmitate | 40% w/w |
| Propylene Glycol Dicaprylate/Dicaprate | 20% w/w |
| Corn Oil | q.s. 100% w/v |

EXAMPLE 7

| | |
|---|---|
| Doramectin | 0.075% w/v |
| BHA | 0.15% w/v |
| Octyl Palmitate | 40% w/w |
| Caprylic/Capric Triglyceride | 20% w/w |
| Corn Oil | q.s. 100% w/v |

I claim:

1. A process for preparing a non-aqueous oral-drench composition which comprises mixing from 0.01% to 2.0% (w/v) of an avermectin compound; from 30% to 45% (w/w) of an oil, said oil being selected from the group consisting of corn oil, sunflower oil, peanut oil and safflower oil; from 0.01% to 1.0% (w/v) of an oil-soluble antioxidant; and from 50% to 70% (w/w) of a fatty acid ester, said fatty acid ester being selected from the group consisting of caprylic/capric triglyceride, octyl palmitate and propylene glycol dicaprylate/dicaprate.

2. The process of claim 1 wherein said oil-soluble antioxidant is butylated hydroxyanisole or butylated hydroxytoluene.

3. The process of claim 1 wherein said oil-soluble antioxidant is butylated hydroxyanisole.

4. The process of claim 1 wherein said composition has a viscosity ranging from 35 to 300 centistokes.

5. The process of claim 1 wherein said composition has a viscosity ranging from 45 to 80 centistokes.

6. The process of claim 2 wherein said avermectin compound is doramectin.

7. A process for preparing a non-aqueous oral-drench composition which comprises admixing from 0.05% to 0.2% (w/v) of an avermectin compound; from 35% to 40% (w/w) of an oil, said oil being selected from the group consisting of corn oil, sunflower oil, peanut oil and safflower oil; from 0.1% to 0.5% (w/v) of an oil-soluble antioxidant, said antioxidant being butylated hydroxyanisole or butylated hydroxytoluene; and from 55% to 65% (w/w) of a fatty acid ester, said fatty acid ester being selected from the group consisting of caprylic/capric triglyceride, octyl palmitate and propylene glycol dicaprylate/dicaprate.

8. The process claim 7 wherein said avermectin compound is doramectin.

9. A method of treating a parasitic disease in a mammal comprising orally administering to a mammal in need of such treatment a therapeutically effective amount of the non-aqueous composition prepared by the process of claim 1.

10. A method of treating a parasitic disease in a mammal comprising orally administering to a mammal in need of such treatment a therapeutically effective amount of the non-aqueous composition prepared by the process of claim 7.

11. The method of claim 9 wherein the avermectin compound is doramectin.

12. The method of claim 10 wherein the avermectin compound is doramectin.

13. A method of treating a parasitic disease in a sheep or cow comprising orally administering to a sheep or cow in need of such treatment a therapeutically effective amount of the non-aqueous composition prepared according to the process of claim 7.

14. The method of claim 13 wherein the avermectin compound is doramectin.

* * * * *

UNITED STATES PATENT AND TRADEMARK OFFICE
CERTIFICATE OF CORRECTION

PATENT NO. : 5,756,474
DATED : May 26, 1998
INVENTOR(S) : KAI-UWE FURSTENAU

It is certified that error appears in the above-identified patent and that said Letters Patent is hereby corrected as shown below:

Claims 1-14 should be deleted to appear as follows:

CLAIMS

1. A non-aqueous oral-drench composition comprising from 0.01% to 2.0% (w/v) of an avermectin compound; from 30% to 45% (w/w) of an oil, said oil being selected from the group consisting of corn oil, sunflower oil, peanut oil and safflower oil; from 0.01% to 1.0% (w/v) of an oil-soluble antioxidant; and from 50% to 70% (w/w) of a fatty acid ester, said fatty acid ester being selected from the group consisting of caprylic/capric triglyceride, octyl palmitate and propylene glycol dicaprylate/dicaprate.

2. The non-aqueous oral-drench composition of claim 1 wherein said oil-soluble antioxidant is butylated hydroxyanisole or butylated hydroxytoluene.

3. The non-aqueous oral-drench composition of claim 1 wherein said oil-soluble antioxidant is butylated hydroxyanisole.

4. The non-aqueous oral-drench composition of claim 1 wherein said composition has a viscosity ranging from 35 to 300 centistokes.

5. The non-aqueous oral-drench composition of claim 1 wherein said composition has a viscosity ranging from 45 to 80 centistokes.

6. The non-aqueous oral-drench composition of claim 2 wherein said avermectin compound is doramectin.

UNITED STATES PATENT AND TRADEMARK OFFICE
CERTIFICATE OF CORRECTION

PATENT NO. : 5,756,474
DATED : May 26, 1998
INVENTOR(S) : KAI-UWE FURSTENAU

It is certified that error appears in the above-identified patent and that said Letters Patent is hereby corrected as shown below:

CLAIMS.

7. A non-aqueous oral-drench composition comprising from 0.05% to 0.2% (w/v) of an avermectin compound; from 35% to 40% (w/w) of an oil, said oil being selected from the group consisting of corn oil, sunflower oil, peanut oil and safflower oil; from 0.1% to 0.5% (w/v) of an oil-soluble antioxidant, said antioxidant being butylated hydroxyanisole or butylated hydroxytoluene; and from 55% to 65% (w/w) of a fatty acid ester, said fatty acid ester being selected from the group consisting of caprylic/capric triglyceride, octyl palmitate and propylene glycol dicaprylate/dicaprate.

8. The oral-drench composition of claim 7 wherein said avermectin compound is doramectin.

9. A method of treating a parasitic disease in a mammal comprising orally administering to a mammal in need of such treatment a therapeutically effective amount of the non-aqueous composition of claim 1.

10. A method of treating a parasitic disease in a mammal comprising orally administering to a mammal in need of such treatment a therapeutically effective amount of the non-aqueous composition of claim 7.

UNITED STATES PATENT AND TRADEMARK OFFICE
CERTIFICATE OF CORRECTION

PATENT NO. : 5,756,474
DATED : May 26, 1998
INVENTOR(S) : KAI-UWE FURSTENAU

It is certified that error appears in the above-identified patent and that said Letters Patent is hereby corrected as shown below:

CLAIMS,

11. The method of claim 9 wherein the avermectin compound administered to said mammal is doramectin.

12. The method of claim 10 wherein the avermectin compound administered to said mammal is doramectin.

13. A method of treating a parasitic disease in a sheep or cow comprising orally administering to a sheep or cow in need of such treatment a therapeutically effective amount of the non-aqueous composition of claim 7.

14. The method of claim 13 wherein the avermectin compound administered to said cow or sheep is doramectin.

Signed and Sealed this

Third Day of November, 1998

*Attest:*

BRUCE LEHMAN

*Attesting Officer*  Commissioner of Patents and Trademarks